United States Patent
Merry et al.

(10) Patent No.: US 7,510,526 B2
(45) Date of Patent: Mar. 31, 2009

(54) MEDICAL DEVICE INFORMATION SYSTEM

(75) Inventors: Randy L. Merry, Woodinville, WA (US); Molly Ciliberti, Sammamish, WA (US); David W. Browne, Thomasville, GA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 216 days.

(21) Appl. No.: 11/027,766

(22) Filed: Dec. 30, 2004

(65) Prior Publication Data

US 2006/0149323 A1 Jul. 6, 2006

(51) Int. Cl.
  *A61B 5/00* (2006.01)
  *A61N 1/39* (2006.01)
(52) U.S. Cl. .......................................... 600/300; 607/5
(58) Field of Classification Search ...................... 607/5; 600/300
  See application file for complete search history.

(56) References Cited

U.S. PATENT DOCUMENTS

| | | | |
|---|---|---|---|
| 4,052,718 A | 10/1977 | Tucci et al. | |
| 5,388,570 A | 2/1995 | Wassil | |
| 5,464,428 A | 11/1995 | Hill | |
| 5,568,123 A | 10/1996 | Derheim | |
| 5,593,426 A * | 1/1997 | Morgan et al. | 607/5 |
| 6,301,501 B1 | 10/2001 | Cronin et al. | |
| 6,694,299 B1 * | 2/2004 | Barrer | 705/8 |
| 6,735,473 B2 | 5/2004 | Kolder et al. | |
| 2003/0212311 A1 * | 11/2003 | Nova et al. | 600/300 |
| 2004/0019258 A1 | 1/2004 | Kavounas et al. | |
| 2004/0030355 A1 * | 2/2004 | Schiller et al. | 607/5 |
| 2004/0049233 A1 | 3/2004 | Edwards | |
| 2004/0055828 A1 | 3/2004 | Kavounas | |
| 2004/0065451 A1 * | 4/2004 | McSheffrey et al. | 169/75 |
| 2004/0128178 A1 * | 7/2004 | Barrer | 705/8 |
| 2004/0155772 A1 | 8/2004 | Medema et al. | |

OTHER PUBLICATIONS

International Search Report and Written Opinion from corresponding PCT Application Serial No. PCT/US2005/046500 mailed on May 12, 2006 (11 pages).

* cited by examiner

*Primary Examiner*—Carl H Layno
*Assistant Examiner*—Yun Haeng Lee
(74) *Attorney, Agent, or Firm*—Shumaker & Sieffert, P.A.

(57) ABSTRACT

In general, the invention is directed to management of information from a plurality of emergency medical devices, such as automated external defibrillators, and associated docking stations. The medical devices and docking stations may communicate with one another and with a remote unit. The managed information includes information pertaining to authorized access and maintenance, inspection indications and inspection certifications. In general, an authorized user can access the emergency medical device without activating alarms that would accompany an emergency. The authorized user can further use the user input interface to enter an inspection certification, which records the inspection, the maintenance performed, the date the device is returned to service, and so forth.

7 Claims, 8 Drawing Sheets

MEDICAL DEVICE INFORMATION SYSTEM

TECHNICAL FIELD

The invention relates to medical devices, and in particular, to collection of data generated by an emergency medical device or associated apparatus.

BACKGROUND

Cardiac arrest is a life-threatening medical condition that may be treated with external defibrillation. External defibrillation includes applying electrodes to the patient's chest to deliver an electric shock to the patient in order to depolarize the patient's heart and restore normal sinus rhythm. The chance that a patient's heart can be successfully defibrillated increase significantly if a defibrillation pulse is applied quickly.

Until recently, individuals such as paramedics, emergency medical technicians, police officers and others trained in defibrillation techniques used defibrillators, but the general public did not. In some cases, the patient's need is urgent and the patient cannot wait for trained personnel to arrive. In recognition of the need for prompt treatment, automated external defibrillators (AEDs) are becoming more commonplace, and are available in venues such as health clubs and auditoriums. In some large venues, such as office buildings, factories, airports and sports arenas, several AEDs may be deployed throughout the venue. In some venues, hundreds of AEDs may be deployed. Ready availability of AEDs may mean that patients may get needed treatment promptly, and need not wait for emergency personnel to arrive. As a result, more lives may be saved.

As part of ordinary security and maintenance procedures, AEDs deployed in a venue may be periodically checked. It is important for the devices to be able to provide therapy in time of need. Checking the devices from time to time helps keep the devices ready provide therapy, by investigating whether the electrodes are in good condition, whether the batteries are charged, and so forth. A responsible person, such as security personnel or a repair person, may be assigned to make an inspection of each AED and to confirm that the device is operational or place the device in an operational condition. The inspection may be relatively simple, because many AEDs perform one or more automatic self-diagnostic routines and provide one or more status indications that the device is operational or in need of service.

As part of the inspection, the responsible person should regularly look at each AED and check the associated status indicators. The responsible person may also be required to prepare and maintain records showing that the inspections have been performed, as well as the status and repair history of the AEDs. In a venue having several AEDs, the cost of inspection may be significant. A deployed AED may be unprepared to provide defibrillation therapy if the responsible person fails to make a proper inspection. In addition, a deployed AED may be unprepared to provide defibrillation therapy if a fault or other problem occurs following an inspection.

Because AEDs may be deployed in venues accessible to the public, AEDs may be prone to mischief or misuse. Theft, inadvertent or inappropriate use, tampering, vandalism and the like may be important concerns. Because of these concerns, AEDs may be deployed with a docking station that deters mischief or misuse. An example of such a docking station is a wall-mounted cabinet with a glass window and an alarm system. The alarm may be triggered when the door of the cabinet is opened or if the AED is removed. Not only does the alarm deter mischief, the alarm also helps summon responding personnel to the site of an emergency.

Many of the concerns applicable to AEDs may be applicable to other emergency medical devices as well. For example, there may be benefits associated with deploying medical devices such as a stroke apparatus, a chest compression device, or a first aid device, throughout a venue. These medical devices, like AEDs, may be inspected as part of ordinary security and maintenance procedures. To deter mischief or misuse, the medical devices may be deployed with docking stations.

SUMMARY

In general, the invention is directed to management of information from a plurality of emergency medical devices, such as AEDs. A system for managing status information may include one or more medical devices associated with one or more docking stations. A medical device, or a docking station, or both, may acquire information and may communicate the information to a remote unit. Such information includes device status information, which pertains to the operating status of the emergency medical devices, the docking stations, or their attendant components.

The invention is further directed to management of information pertaining to authorized access and maintenance, inspection indications, inspection certifications, and the locations of medical devices within the system. The remote unit serves as a status monitor that provides a central point for collecting, aggregating and recording information about authorized maintenance, inspection indications, inspection certifications, and the locations of the medical devices.

When an authorized user wishes to access an emergency medical device for some reason other than an emergency, such as maintenance, the invention enables the authorized user to be proximate to an emergency medical device and to enter an authorization into a user input interface. When the authorization is validated, the authorized user can access the emergency medical device without activating alarms that would accompany an emergency. The authorized user can further use the user input interface to enter an inspection certification, which records the inspection, the maintenance performed, the date the device is returned to service, and so forth. The remote unit receives the inspection certification and updates a service log that records each device's service history.

In addition, the invention supports management of patient status information, which is information pertaining to treatment of a patient. In the case of an AED, for example, patient status information can include data such as information about the patient's heart rate and rhythm, whether defibrillation therapy was delivered to the patient, the number of defibrillation shocks delivered, the quantity of energy per shock, and the response of the patient to the therapy. After the emergency medical device has been replaced in the docking station following an emergency, the emergency medical device communicates the patient status information to the remote unit. The emergency medical device can initiate the communication on its own or in response to an interrogation. The remote unit, upon receiving the patient status information, can relay the patient status information to the medical facility that will receive the patient.

The invention also supports tracking an emergency medical device that is removed from its docking station. The emergency medical device may include a trackable element, such as a radio frequency identification (RFID) tag or a radio transmitter, that can be sensed by a tracking element such as a RFID tag detector or a radio range detector. The docking station can include a tracking element, and a plurality of tracking elements can also be deployed around the venue. The tracking elements generate tracking signals that are communicated to the remote unit, which can determine the location of the emergency medical device. This location can further be supplied to responders such as emergency medical technicians.

The invention is not limited to systems in which every medical device is associated with a docking station. For practical reasons that will be described in more detail below, however, it may be advantageous for a medical device to be associated with a docking station. It may further be advantageous for the medical device and the docking station to communicate with one another. The communication may involve interrogations for status information, as well as status information itself.

In one embodiment, the invention is directed to a method that may be practiced by an emergency medical device. The method comprises acquiring patient status information pertaining to treatment of a patient with an emergency medical device. The method also comprises, after the emergency medical device is placed in a docking station, establishing communication with a remote unit via a communication network and communicating the patient status information from the emergency medical device to the remote unit. The patient status information may be communicated to the remote unit via the docking station.

In another embodiment, the invention presents a device comprising a docking element configured to retain an emergency medical device, a sensor element configured to detect removal of the emergency medical device from the docking element, and a user input interface configured to receive an authorization from a person proximate to the device. The device also includes a processor configured to communicate an emergency message to a remote unit when the removal of the emergency medical device from the docking element is unaccompanied by the authorization, and further configured to communicate an administrative message to the remote unit when the removal of the emergency medical device from the docking element is accompanied by the authorization. The device can also include a tracking element configured to generate a tracking signal as a function of the position of the emergency medical device with respect to the device.

In a further embodiment, the invention is directed to a device comprising an electrical source configured to generate a shock to defibrillate a heart, at least two electrodes configured to deliver the shock to the heart, and a trackable element configured to generate a trackable signal to a tracking element less than one kilometer from the device. The trackable element can be, for example, an RFID tag.

In an additional embodiment, the invention is directed to a device comprising a docking element configured to retain an emergency medical device and a communication module. The communication module is configured to receive patient status information from the emergency medical device when the emergency medical device is placed in the docking element. The communication module is further configured to communicate the patient status information to a remote unit.

In another embodiment, the invention is directed to a system comprising an emergency medical device comprising a trackable element. The system also includes a plurality of tracking elements, each tracking element configured to detect the trackable element within a range of less than one kilometer and further configured to generate a tracking signal as a function of the detection. The system also includes a network coupled to the tracking elements configured to receive at least one tracking signal and to communicate the tracking signal to a remote unit.

A further embodiment presents a method that that may be practiced by a docking station. The method includes receiving in a docking element an emergency medical device and receiving an inspection certification from the emergency medical device. The method can also include communicating the inspection certification from the docking station to a remote unit.

In an added embodiment, the invention is directed to a method that may be practiced by an emergency medical device. The method comprises establishing communication with a remote unit via a communication network after being placed in a docking station, and communicating an inspection indication to the remote unit. The inspection indication requests a physical inspection for an emergency medical device placed in the docking station. In another embodiment, the invention is directed to a method that may be practiced by a docking station, comprising receiving in a docking element an emergency medical device, and communicating an inspection indication to the remote unit.

In another embodiment, the invention presents a method comprising receiving a medical device in a docking element, interrogating the medical device for patient status information pertaining to treatment of a patient, receiving the patient status information, and communicating the patient status information to a remote unit. A docking station can practice this embodiment of the invention.

In a further embodiment, the invention is directed to a method comprising receiving an authorization and deactivating an alarm triggered by access to an emergency medical device when the authorization is valid. A docking station can practice this embodiment of the invention.

Further embodiments of the invention are directed to computer-readable media that include instructions for causing a programmable processor to carry out the methods described above.

The invention may offer one or more advantages. The invention may be practiced with systems of many configurations. Any number of docking stations and medical devices may be tracked, monitored and maintained with the invention. The invention may also be practiced with any number of networks, and may in some cases be integrated into an existing network in the venue, such as a security network or a private building maintenance network.

The invention provides easy monitoring of any number of medical devices and docking stations deployed throughout a venue. Numerous features of the invention may allow a person responsible for inspection to record the inspection at the docking station. The invention simplifies record keeping operations, such as maintenance of a status log.

In the event of a problem with any device in the system, the invention facilitates prompt notification of a responsible person. The invention facilitates resolution of the problem by enabling authorized inspections without setting off false alarms. The invention offers the further benefit of receiving and recording inspection certifications when the problems are resolved.

In an emergency, the invention advantageously supports tracking of the emergency medical device. In general, determining the location of the device is associated with determining the location of the patient. As a result, a remote unit that notifies a person about the location of the emergency medical device also provides information about the site of the emergency.

In addition, the device may acquire important status information pertaining to the patient during the emergency, such as vital signs, heart rhythm, administered therapies, and the like. This patient status information can be quickly relayed to a medical facility that receives the patient. The result is more complete medical records for the patient, and more complete information for the patient's physician.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
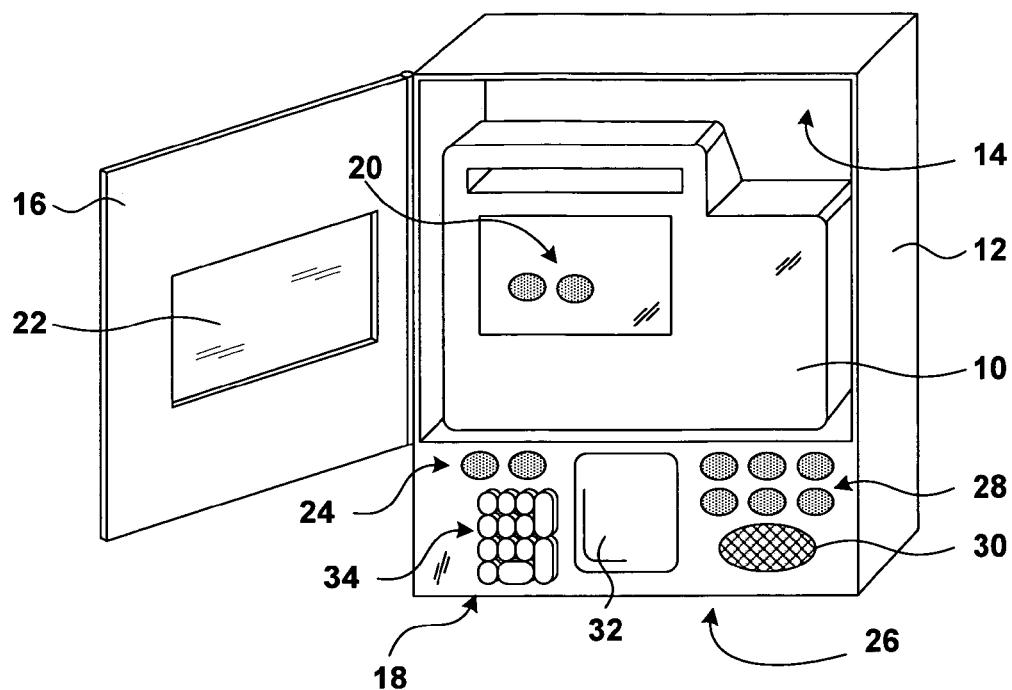
FIG. 1 is a perspective drawing of an automated external defibrillator in a cabinet docking station according to an embodiment of the invention.

FIG. 1 is a perspective drawing of an automated external defibrillator (AED) 10 in an exemplary docking station 12. AED 10 and docking station 12 are illustrative of the practice of the invention, and for simplicity, the invention will be described in terms of AEDs and docking stations. The invention is not limited to docking stations and AEDs, however, but may include other devices including other types of emergency medical devices including physiological monitors, such as a blood pressure monitor or a capnograph. Other examples of emergency medical devices include chest compressors, cooling garments, oxygen delivery apparatus and the like.

In the example of FIG. 1, docking station 12 is a cabinet, comprising a compartment 14 that receives AED 10 and a hinged door 16 that closes to secure AED 10 inside compartment 14. AED 10 is portable. When an operator needs to use AED 10, the operator opens door 16 and lifts AED 10 from compartment 14. Cabinet 12 also includes a base 18, which supports AED 10 and houses other components described below.

AED 10 is capable of administering defibrillation therapy to a patient. AED 10 includes an electrical source (not shown) that can generate one or more shocks to defibrillate the heart of a patient. The shocks may be delivered to the patient via two electrodes (not shown), which may be hand-held electrode paddles or adhesive electrode pads placed externally on the skin of the patient.

The electrodes may be packaged in a sealed pouch (not shown), such as an airtight foil bag, which protects the electrodes from the environment. The electrodes may include substances that may degrade or dry out when exposed to air. For example, the electrodes may include a hydrogel layer that hydrates the patient's skin, forms an interface with the patient, promotes adhesion of the electrodes to the skin and reduces the risk of burns. The electrodes may be stored in a pouch to prevent the hydrogel from drying out and losing its desirable properties. The pouch may be stowed inside AED 10 or inside cabinet 12.

An operator using AED 10 use typically brings AED 10 to the patient, opens the pouch, retrieves the electrodes and places the electrodes in the correct positions on the patient's chest. In some models of AED 10, the operator may also couple the electrodes to AED 10 by plugging an electrical connector into a receptacle on AED 10.

Electrodes of the kind described above are intended for use on one occasion. Following use, the electrodes are discarded, and AED 10 is supplied with a fresh pouch that holds fresh electrodes. Even if the electrodes are not used, however, the electrodes may have a shelf life. As a precaution, the pouch should be replaced when the shelf life expires.

AED 10 may include an internal power source (not shown). The power source for many models of AED 10 is a battery, although some models of AED may be capable of being "line powered," i.e., plugged into an electrical outlet. Battery power is advantageous in many respects. First, in many situations, the patient may be far from an electrical outlet. In those situations, AED 10 may rely upon a battery to supply the energy for the defibrillation shocks. Second, a power supply in the form of a battery makes AED 10 portable and useful in a wider variety of emergency situations.

AED 10 also comprises an energy storage device (not shown), such as one or more capacitors, and a charging circuit (not shown), such as a flyback charger. When a defibrillation shock is needed, the charging circuit transfers energy from the power supply to the energy storage device. When the energy stored in the energy storage device reaches a desired level, AED 10 is ready to deliver defibrillation therapy. The therapy may be delivered automatically or manually.

AED 10 typically includes one or more processors, such as a microprocessor or application specific integrated circuit (not shown), that control various functions of AED 10. In some devices, the processor governs charging of the energy storage device, for example, and evaluates heart rhythms of the patient sensed via the electrodes. The processor can, in some models, deliver the defibrillation shocks automatically. The processor is further configured to execute a routine that performs a self-diagnostic test of AED 10 and that acquires device status information as a function of performing the self-diagnostic routine.

Status information pertains to the operating status of AED 10 and its attendant components. Device status information may include, for example, data indicative of AED 10 being in good working order. Device status information may also include data indicative of a fault or potential problem with AED 10, such as data indicative of a failed or damaged component. Data indicating that the battery is low, or that the battery is failing to hold a charge, are additional examples of AED device status information. Device status information may also include data indicating that the electrodes or other components are nearing the end of their shelf life.

AED 10 may include one or more output elements 20 that convey device status information to a person. As shown in FIG. 1, output elements 20 include visual annunciators, such as light-emitting diodes (LEDs) that illuminate or darken to convey device status information. Output elements 20 may, for example, indicate whether AED 10 is in good working order, whether the battery is ready, or whether AED 10 needs service. Output elements 20 may include other or additional annunciators, such as a liquid crystal display (LCD), a cathode ray tube (CRT) display, a strobe, or a speaker that is capable of delivering an audible signal or a spoken message.

Hinged door 16 of cabinet 12 includes a window 22. When AED 10 rests in compartment 14 and door 16 is closed, output elements 20 may be visible through window 22. Base 18 of cabinet 12 also includes AED status output elements 24 that may be redundant of output elements 20 on AED 10. In other words, output elements 24 of cabinet 12 may convey the same device status information as output elements 20 of AED 10. Output elements 24 may also convey AED status information in a different way than that conveyed by AED 10. Cabinet 12 may, for example, employ a simplified "OK-NOT OK" indicator system, while AED output elements 20 may be more specific about the nature of any problems.

The redundant presentation of status information may be advantageous in several respects. First, instead of facilitating observation of output elements 20 on AED 10, window 22 may impede observation of output elements 20. Because AED 10 may be recessed in compartment 14, for example, output elements 20 may not be visible through window 22 from all angles. Further, window 22 may be cracked or dirty or reflective of light sources that wash out the visual annunciators. Output elements 24 on cabinet 12 may also be larger or brighter than output elements 20 on AED 10, allowing the device status information to be perceived from a greater distance or from a wider angle of view. Thus, a person wishing to perform a routine visual check on the status of AED 10 may obtain status information about AED 10 more readily by observing output elements 24 on cabinet 12.

Cabinet 12 presents device status information via output elements 24 upon receiving the status information from AED 10. As will be described in more detail below, AED 10 may establish a communication link with cabinet 12, and may communicate device status information to cabinet 12. The communication link may be, but need not be, wireless.

In addition to AED status output elements 24, base 18 includes docking station status output elements 26. Docking station status output elements 26 may include visual annunciators 28, a speaker 30 and a display screen 32. Visual annunciators 28 may comprise, for example, LEDs, a strobe or a warning light. Display screen 32 may comprise, for example, an LCD or CRT display.

Docking station status output elements 26 convey status information that is not redundant of status information conveyed by AED status output elements 24. The status information conveyed by docking station status output elements 26 may include status information pertaining to AED 10, status information pertaining to cabinet 12, or status information pertaining to other AEDs. As will be described below, AED 10, or cabinet 12, or both, may be part of a networked system of AEDs, and the status information conveyed by docking station status output elements 26 may include status information pertaining to the networked system of AEDs.

Visual annunciators 28 may convey, for example, that cabinet 12 is in good working order, or that the communication interfaces of cabinet 12 are working properly. Speaker 30 may convey, for example, an alarm signaling that door 16 is open or ajar, or verbal instructions concerning use of AED 10 or cabinet 12. Display screen 32 may convey any information in text or visual form, such as a pictorial instruction for opening door 16, or a text warning that AED 10 is out of service, along with directions for finding the nearest AED in the network that is in service.

In the embodiment shown in FIG. 1, base 18 also includes a user input interface 34. A user proximate to cabinet 12 uses user input interface 34 to enter data into cabinet 12. Although user input interface 34 is depicted in FIG. 1 as a numerical keypad, the invention also supports inclusion of a user input interface in the form of an alphanumeric keypad, touch screen, pointing device, selection buttons, and the like.

Data entered via user input interface 34 can serve a number of functions. For example, a user can enter an authorization to remove AED 10 from cabinet 12 for maintenance purposes. In an emergency, it will not be necessary for a user to enter any authorization, and a user can retrieve AED 10 by opening the door 16 of cabinet 12 and removing AED 10. Cabinet 12 can include a sensor element configured to detect opening of door 16 or removal of AED 10 from cabinet 12, so that such actions trigger an alarm, thereby alerting responsible personnel to the emergency. Maintenance personnel may desire to open door 16 or remove AED 10 without triggering any alarm. Accordingly, one function for user input interface 34 is to receive an authorization, such as a code or password, which allows a user to have access to AED 10 without triggering an alarm locally.

In addition, as described below, cabinet 12 includes a processor that is configured to communicate with a remote unit. The processor is configured to communicate an emergency message to the remote unit when the removal of AED 10 from cabinet 12 is unaccompanied by a valid authorization. Cabinet 12, or the remote unit, or both, can determine whether the authorization is valid. When access to AED 10 is accompanied by a valid authorization, the processor can be configured to communicate an administrative message to the remote unit, notifying the remote unit that authorized personnel have obtained access to AED 10. In addition, cabinet 12, or the remote unit, or both, can deactivate alarms in response to a valid authorization.

User input interface 34 can also be used to receive device status information about the condition of AED 10 or cabinet 12 or both. The device status information can pertain to the operating status of AED 10 and its attendant components. For example, when maintenance personnel replace defibrillation electrodes that are included with AED 10, maintenance personnel can enter a code via keypad 34 that verifies that the defibrillation electrodes have been replaced.

Upon entry of device status information via user input interface 34, the processor in cabinet 12 is configured to communicate the device status information to the remote unit. As described below, this device status information can be recorded by the remote unit as a service record that indicates what maintenance had been done to AED 10 or cabinet 12, by whom, and when. The remote unit can further use the device status information to determine whether a service call is in order. A service call may be in order when, for example, regular maintenance personnel are unable to put AED 10 in a working condition such that AED 10 can be returned to active service. A service call summons a specialist who can return AED 10 to a working condition.

A further use for user input interface 34 is to receive an inspection certification. AED 10 may be routinely inspected by an inspector, who can certify that AED 10 is in condition for use or who can determine that maintenance is in order. When AED 10 undergoes a routine in-person inspection, the inspector can certify that the inspection has been completed via user input interface 34. The inspection certification can be in the form of a code or password. In addition, the inspector can attest to the work by entering an identification code that identifies the inspector and that confirms the inspection. The processor in cabinet 12 is configured to communicate the identification code and the inspection certification to the remote unit, which validates the identification code and the inspection certification to determine whether the inspection certification is valid or invalid. When the identification code and the inspection certification are valid, the remote unit records the inspection certification as part of the service record for the AED.

Figure 2:
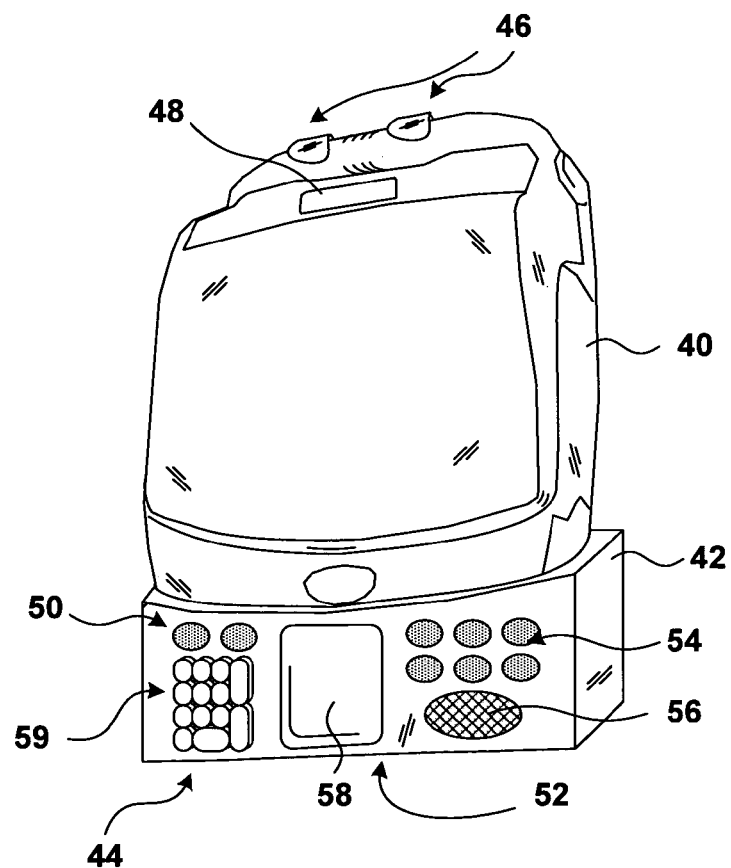
FIG. 2 is a perspective drawing of an automated external defibrillator in a bracket docking station according to another embodiment of the invention.

FIG. 2 is a perspective drawing of another AED 40 in another exemplary docking station 42. In FIG. 2, docking station 42 is a wall-mounted bracket, rather than a cabinet. Bracket 42 includes a shaped base 44 that receives AED 40 and supports AED 40. Bracket 42 also includes and clasps 46, which, in cooperation with base 44, retain AED 40 and secure AED 40 to bracket 42. Clasps 46 may be flexible. When an operator needs to use AED 40, the operator may pull AED 40 from clasps 46 and lift AED 40 out of base 44. Bracket 42 can include a sensor element configured to detect removal of AED 40, which can trigger an alarm indicating an emergency.

AED 40 may include one or more output elements 48 that convey device status information about AED 40, and base 44 may include AED status output elements 50 that may be redundant of output elements 48. As will be described in more detail below, AED 40 may establish a communication link with bracket 42. AED 40 may communicate status information to bracket 42, which bracket 42 may present via output elements 50 on base 44.

Output elements 48 and 50 may be similar to output elements 20 and 24 shown in FIG. 1. Although output elements 48 are not recessed in a compartment or obscured by a window, output elements 48 may be small or difficult to read at a distance. Output elements 50 may be more easily perceived from a greater distance or from a wider angle of view, allowing a person to readily obtain status information about AED 40.

Base 42 includes docking station status output elements 52. Like docking station status output elements 26 shown in FIG. 1, docking station status output elements 52 may include visual annunciators 54, a speaker 56 and a display screen 58. Base 42, as depicted in FIG. 2, also includes a user input interface 59, which depicted in FIG. 2 as a keypad. User input interface 59 can be similar in form and function to user input interface 34 depicted in FIG. 1. In particular, user input interface 59 can be used to enter data such as authorizations and inspection certifications.

The embodiments of an AED and a docking station shown in FIGS. 1 and 2 are for purposes of illustration. The invention is not limited to the arrangements depicted. For example, the invention encompasses embodiments in which the docking station output elements are positioned above the AED, or on multiple sides of the AED. The invention encompasses embodiments that include more or fewer output elements than are shown. The invention also encompasses embodiments that include docking elements to retain the AED other than clasps, shaped bases, cabinets and doors. Docking elements may include clamps, lids, covers, trays, shelves, drawers, latches, and the like.

Figure 3:
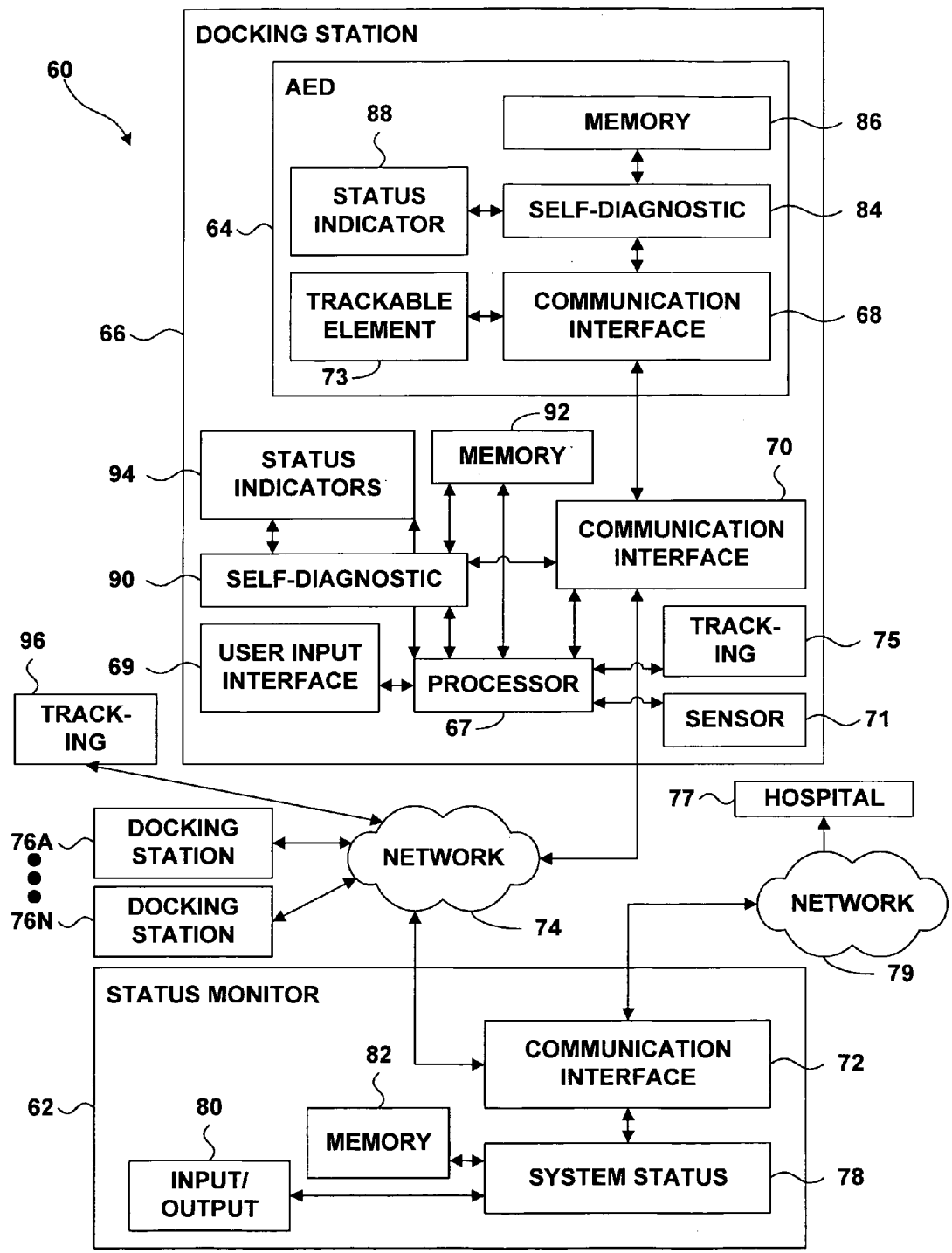
FIG. 3 is a block diagram illustrating a system for managing information from a plurality of medical devices such as AEDs and docking stations, according to an embodiment of the invention.

FIG. 3 is a block diagram illustrating an example system 60 in which a status monitor 62 receives status information, which can include device status information and patient status information, from an AED 64 and a docking station 66. AED 64 and docking station 66 may be either of the embodiments depicted in FIGS. 1 and 2, but are not limited to those embodiments.

In the embodiment of system 60 shown in FIG. 3, status monitor 62 is a unit that is remote from AED 64 and docking station 66, but is in two-way communication with AED 64 and docking station 66. Status monitor 62 may transmit an interrogation for device status information to AED 64 or docking station 66. AED 64 or docking station 66 may perform a self-diagnostic routine to acquire the device status information, and may communicate the status information to status monitor 62.

In system 60, AED 64 does not communicate with status monitor 62 directly. Rather, AED 64 communicates with status monitor 62 via docking station 66. In particular, AED 64 includes a communication interface 68 that establishes a communication link with a communication interface 70 in docking station 66. Communication interface 70 in turn establishes a communication link with a communication interface 72 in status monitor 62 over a network 74. Similarly, interrogations from status monitor 62 to AED 64 are communicated through docking station 66.

Network 74 may be any network. Network 74 may comprise, for example, a public switched telephone network, a cellular telephone network, a local area network, a wide area network, a global computer network such as the Internet, an integrated services digital network, or the like. In some venues in which AED 64 and docking station 66 may be deployed, the venue may include a dedicated security network or a private building maintenance network. Either may serve as network 74. Network 74 may include hard-wired electrical or optical communication links, wireless links, or a combination of both.

Docking station 66 includes a processor 67, such as a microprocessor, microcontroller, digital signal processor or application specific integrated circuit. Processor 67 can be configured to perform a number of functions, such as controlling communication with status monitor 62. For example, processor 67 can validate authorizations entered via user input interface 69, and can detect removal of AED 64 from docking station 66 or replacement of AED 64 in docking station 66 via sensor 71. When replacement is detected, processor 67 can be configured to communicate interrogation for device status information to AED 64. In some embodiments, processor 67 is configured to evaluate the device status information to determine whether AED 64 is in a condition to be returned to service, and to generate an inspection indication when the device status information indicates that AED 64 may not be in a condition to be returned to service. In general, the inspection indication is a request for a physical, in-person inspection for AED 64. As discussed below, AED 64 may also generate an inspection indication.

Processor 67 can also communicate an emergency message to status monitor 62 when the removal of AED 64 from docking station 66 is unaccompanied by a valid authorization, and can further communicate an administrative message to status monitor 62 when the removal of AED 64 is accompanied by a valid authorization. Processor 67 can further activate or deactivate local alarms in response to a valid authorization. In addition, processor 67 can be configured to validate and communicate an inspection certification to status monitor 62.

User input interface 69 can be any element that receives data locally. User input interface 69 can be a device such as a numerical keypad, an alphanumeric keypad, a touch screen, a pointing device, one or more selection buttons, and the like.

Sensor 71 can be any element that senses the presence, absence, removal or replacement of AED 64. Sensor 71 can be, for example, an electrical switch, a pressure sensor, a weight sensor, an acoustic sensor, or an optical sensor. Sensor 71 provides a signal to processor 67 that indicates the physical presence of AED 64 to docking station 66. In some embodiments of the invention, AED 64 includes a sensor (not shown) that enables AED 64 to determine whether AED 64 has been removed from or replaced in docking station 66.

In the embodiment shown in FIG. 3, AED 64 includes a trackable element 73 and docking station 66 includes a tracking element 75. Trackable element 73 can be any wireless element that can be passively or actively tracked by a tracking element, including but not limited to, tracking element 75 in docking station 66.

One exemplary embodiment of trackable element 73 can be a radio frequency identification (RFID) tag, and an exemplary embodiment of tracking element 75 can be a stationary RFID detector. An RFID tag is a wifeless electronic device that includes an integrated circuit and a coil. The coil may act as a source of power, as a receiving antenna, and a transmitting antenna. The integrated circuit may include wireless communications components and memory. The RFID detector includes an antenna and a transceiver, and "interrogates" an RFID tag by directing an interrogating electromagnetic signal to the RFID tag. The RFID tag, which receives power from interrogating signal, responds to the interrogation and transmits a responsive electromagnetic signal to the RFID detector. An RFID detector typically has a range or "read area" in which the strength of the interrogating signal is sufficient to power the RFID tag and to cause generation of a responsive signal. A typical read area has a radius of a few meters.

Trackable element 73 need not be embodied as an RFID tag, however. In some embodiments, trackable element 73 comprises a battery-powered radio transmitter. In this embodiment, tracking element 75 comprises a range detector that senses the strength of the signal transmitted from the transmitter.

In general, tracking element 75 monitors trackable element 73, and generates a tracking signal as a function of the position of AED 64 with respect to stationary docking station 66. Tracking element 75 can be dormant until triggered by removal of AED 64 from docking station 66, as sensed by sensor 71. When a user removes AED 64, tracking element 75 becomes active and generates a tracking signal. The tracking signal can provide information about the distance of AED 64 from docking station 66, as well as the direction of displacement. Docking station communicates the tracking signal or other information about the location of AED 64 to status monitor 62. As will be described below, the invention encompasses embodiments in which other tracking elements 96 deployed in a venue track the position of AED 64 through the venue, and each of these tracking elements may likewise communicate a tracking signal or other information about the location of AED 64 to status monitor 62 via network 74. In this way, status monitor 62 can track the location of AED 64 as AED 64 passes in proximity to tracking elements.

Generally speaking, the range of tracking elements is short. The useful range between a tracking element and a trackable element is usually less than one kilometer from the device and is typically much less than one kilometer. Prudent deployment of medical devices and docking stations in a venue normally places the medical devices within reasonable proximity of any potential emergency, so long-range tracking capability, such as the tracking capability of a global positioning system, is not warranted. In addition, some long-range tracking technologies are not suitable for tracking in an indoor venue.

When AED 64 is removed from docking station 66 without entry of a valid authorization via user input interface 69, it is possible that AED 64 will be used to monitor and provide therapy to a patient. In the event AED 64 is so used, patient status information may be recorded in memory 86. Patient status information includes, but is not limited to, information pertaining to cardiac signals sensed from the patient. Information pertaining to cardiac signals includes information about the patient's heart rate and rhythm. Patient status information further includes, but is not limited to, whether defibrillation therapy was delivered to the patient, the number of defibrillation shocks delivered, the quantity of energy per shock, and the response of the patient to the therapy.

When AED 64 is placed in docking station 66, AED 64 communicates the patient status information to status monitor 62. The communication can be initiated by AED 64. The communication can also be prompted by docking station 66 when sensor 71 detects the return of AED 64. Status monitor 62 can communicate the patient status information to a hospital 77 or other medical facility by a communication network 79, such as a telephone or radio network. In this way, medical facility 77 that receives the patient can learn about the patient's condition and applied therapies. Although networks 74 and 79 are depicted as separate elements, the invention supports embodiments in which a single network is employed.

In the event AED 64 was not used, AED 64 can communicate to status monitor 62 that no patient status information has been recorded. In addition, AED 64 can communicate inspection indication to status monitor 62. AED 64 can communicate inspection indication even if AED 64 was not used. The purpose of the inspection indication is to request a physical inspection of AED 64. An in-person physical inspection of AED 64 can provide further assurance that AED 64 is fit to return to service by inspecting for damage, checking electrodes, and so forth.

System 60 is not limited to a single AED 64 or a single docking station 66. Other docking stations 76A-76N may communicate with remote status monitor 62 via network 74. In particular, status monitor 62 may receive device status information or patient status information from docking stations 76A-76N and from AEDs (not shown) associated with docking stations 76A-76N. Status monitor 62 may also transmit interrogations to docking stations 76A-76N and the associated AEDs. AED 64 and docking station 66 are representative of other AEDs and docking stations in system 60.

System status module 78 in status monitor 62 provides a central point for collecting, aggregating and recording device status information pertaining to AEDs and docking stations in system 60. Status monitor 62 further provides a central point for collecting, aggregating and recording information about authorized maintenance, inspection certifications, and the locations of medical devices within system 60. Status monitor 62 further collects patient status information, as described below. In this way, system status module 78 monitors the AEDs and docking stations in system 60. System status module 78 is a processor that may summarize the information and present the information via an input/output device 80. In addition, system status module 78 may interrogate one or more AEDs or one or more docking stations in system 60, and may present to a person information received in response to the interrogation via input/output device 80. Input/output device 80 may comprise one or more display screens, keyboards, audible alarms, LEDs, LCDs, printers, touch screens, pointing devices, and the like. Input/output device 80 may also comprise a communication device configured to establish a communication link with another person or device not shown in FIG. 3. For example, when device status information from AED 64 indicates at problem that may require a professional service call, input/output device 80 may automatically summon the service provider.

System status module 78 may further store information pertaining to the status of system 60, or any AEDs or docking stations in system 60, in memory 82. Information stored in memory 82 may include, for example, routine device status information, data pertaining to repair histories, and tracking data showing the locations of devices. Memory 82 also stores patient status information when AED 64 monitors or delivers therapy to a patient.

In a typical venue, system status module 78 is remote from AEDs or docking stations in system 60. AEDs and docking stations are ordinarily readily accessible, and in some venues, may be accessible to members of the general public. System status module 78, by contrast, is typically housed in a secure location and is not readily accessible.

In one illustrative embodiment, a personal computer may operate as system status module 78, input/output device 80, and memory 82. In another illustrative embodiment, a portable device such as a pager or personal digital assistant (PDA) may operate as input/output device 80, with system status module 78 and memory 82 located in a different physical location. In this embodiment, system status module 78 and input/output device 80 may communicate via a communication link such as a wireless link or a telephone line. System status module 78 and input/output device 80 may also communicate over network 74.

A responsible person, such as a security supervisor, may observe the status of any AED or docking station in system 60 by observing input/output device 80. Input/output device 80 may notify the responsible person that all AEDs and docking stations in system 60 are operational, for example, or may notify the responsible person when an AED or a docking station in system 60 is in need of attention. When an AED or a docking station in system 60 is in need of attention, input/output device 80 may present the responsible person with information such as the location of the device in question and the nature of the problem. Input/output device 80 may further present the responsible person with status information received from the device in response to an interrogation by system status module 78. Input/output device 80 may also present the responsible person with data stored in memory 82, such as the repair history of the device in question.

AED 64 includes a self-diagnostic module 84 that monitors the status of AED 64. Self-diagnostic module 84 is a processor that executes one or more self-diagnostic routines. The self-diagnostic routines may be initiated by self-diagnostic module 84, or may be initiated in response to a change in the condition of AED 64, such as a component malfunction. By execution of a self-diagnostic routine, self-diagnostic module 84 performs one or more internal self-tests to acquire device status information about the state of readiness of AED 64. Self-diagnostic module 84 may evaluate and identify matters that can be customer serviceable, such as battery or electrode replacement, and matters that may require a professional service call. AED 64 may record the device status information in memory 86, and may present some or all of the status information via one or more status indicators 88. When the results of the self-tests indicate that AED 64 is ready for use, for example, status indicators 88 may provide a visible or audible indication of readiness. Status indicators 88 may comprise any of output elements 20 or 48 described in connection with FIGS. 1 and 2.

AED 64 may further communicate the status information to docking station 66 via communication interfaces 68 and 70. Communication between AED 64 and docking station 66 may be by any communication technique. In the embodiment shown in FIG. 3, AED 64 and docking station 66 may engage in two way communication, thereby enabling AED 64 to receive an interrogation from status monitor 6 or docking station 66.

Communication between AED 64 and docking station 66 may be in accordance with one or more wireless communication techniques. For example, one communication protocol, commonly referred to as Bluetooth, uses short-range 2.4 GHz radio technology employed to transport data between devices. Other possible communication protocols include IEEE 802.11a, 802.11b, and 802.11g, which are industry standard protocols for wireless networking. Yet another possible protocol is HomeRF, which was initially designed for wireless communications between devices and appliances within a home.

Communication between AED 64 and docking station 66 may also communicate via a physical communication link. When docking station 66 receives AED 64, mating electrical or optical components in docking station 66 and AED 64 may engage, thereby enabling communication. In addition, AED 64 and docking station 66 may communicate via a combination of wireless and physical communication links. Wireless links and physical communication links both may be implemented so that AED 64 may be quickly and easily removed from docking station 66 without hindrance.

Docking station 66 includes a self-diagnostic module 90 that monitors the status of docking station 66. Self-diagnostic module 90 is a processor that executes a self-diagnostic routine to perform internal self-tests and to acquire status information about docking station 66. The self-diagnostic routines may be initiated by self-diagnostic module 90 or may be initiated in response to a change in the condition of docking station 66. Self-diagnostic module 90 may evaluate and identify matters that can be customer serviceable and matters that may require a professional service call.

In addition, self-diagnostic module 90 may collect, aggregate or interpret status information received from AED 64. In some circumstances, self-diagnostic module 90 may use device status information from AED 64 and from self-tests to pinpoint the source of a problem. Self-diagnostic module 90 may record the status information in memory 92, and may present some or all of the status information via one or more status indicators 94. Status indicators 94 may include AED status output elements 24, such as AED status output elements 24 and 50 in FIGS. 1 and 2, that convey AED status information redundantly. Status indicators 94 may also include output elements such as docking station status output elements 26 and 52 in FIGS. 1 and 2. Status indicators 94 may convey status information pertaining to AED 64, status information pertaining to docking station 66, or status information pertaining to other AEDs or docking stations in system 60.

Docking station 66 further includes a power source (not shown in FIG. 3). Unlike AED 64, which is portable and is usually battery-powered, docking station 66 is stationary and may be line-powered. System 60 may include several docking stations 66, 76A-76N deployed throughout a venue, and the docking stations may be wall-mounted or otherwise located for access to the power grid. The invention is not limited to line-powered docking stations, however, but includes docking stations having power sources such as batteries or solar cells.

An advantage of system 60 shown in FIG. 3 is an efficient use of energy. It may be undesirable to devote too much energy from the power supply in AED 64 to communication with docking station 66 or status monitor 62. AED 64 may be battery powered, and the battery power may be needed to supply the energy that may be delivered to a patient as a lifesaving defibrillation shock. Accordingly, the communication resources of AED 64 may be scaled back. When AED 64 is engaged with docking station 66, such as is depicted in FIGS. 1 and 2, AED 64 may not need to expend much energy to communicate with docking station 66.

Docking station 66, by contrast, does not need to conserve energy to provide defibrillation therapy. Moreover, a line-powered docking station 66 may be relieved of the energy constraints that affect a battery-powered AED 64. Accordingly, docking station 66 may devote more energy to communication. In system 60, docking station 66 is responsible for communicating with status monitor 62 and for supplying status monitor 62 with status information about AED 64 and docking station 66. Docking station 66 is also responsible for receiving interrogations from status monitor 62 and relaying interrogations to AED 64.

Figure 4:
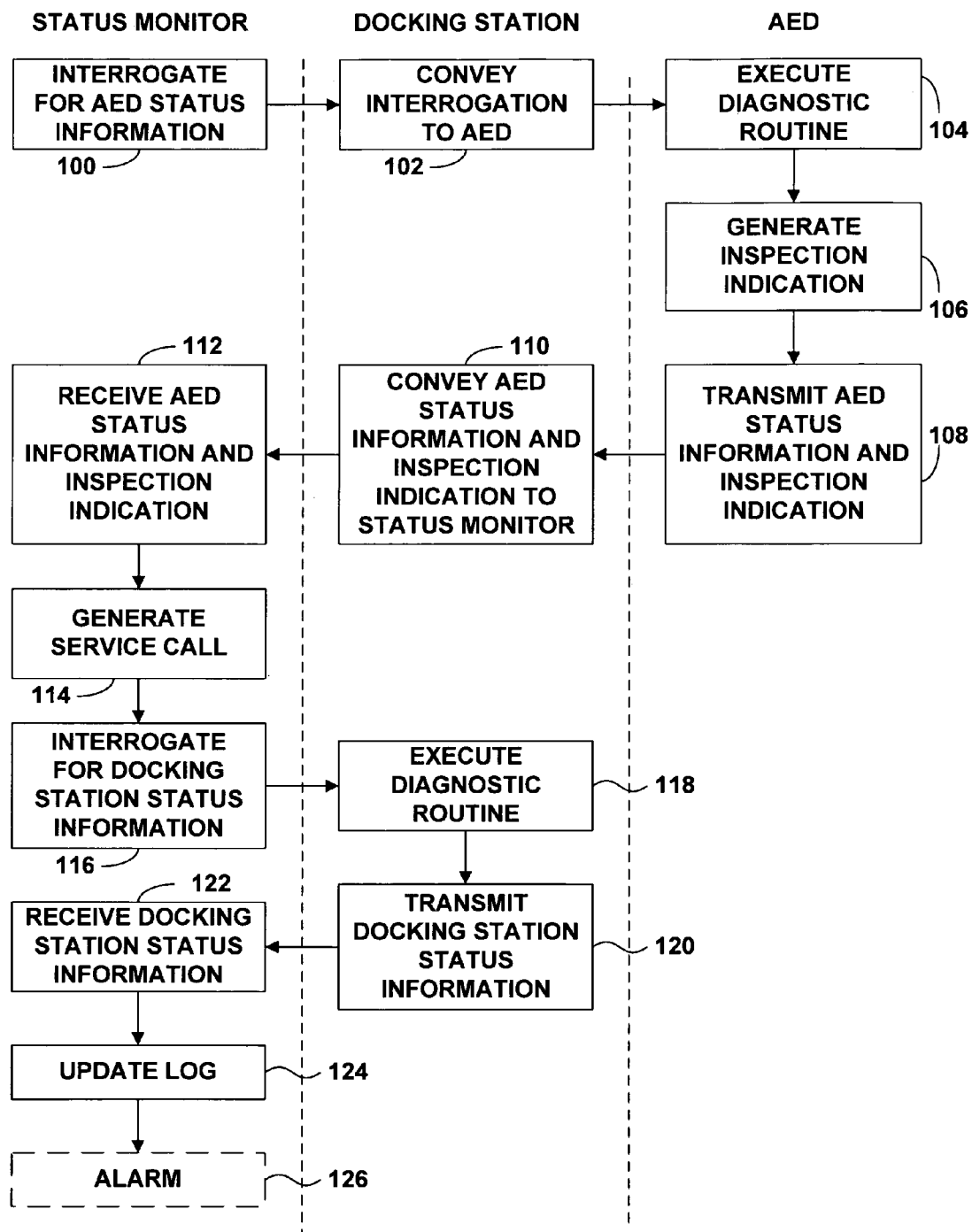
FIG. 4 is a flow diagram illustrating interrogation of a medical device according to an embodiment of the invention.

FIG. 4 is a flow diagram illustrating an interrogation in a system such as system 60 in circumstances in which no emergency is known to exist. Status monitor 62 interrogates AED 64 by transmitting an interrogation for status information (100). Status monitor 62 may initiate the interrogation in response to a command from a responsible person, or status monitor 62 may initiate the interrogation automatically. An automatic interrogation may be part of a routine periodic interrogation, for example, or the automatic interrogation may be in response to status information received from AED 64, docking station 66 or another device in system 60.

Docking station 66 receives the interrogation and communicates the interrogation to AED 64 (102). In response, the self-diagnostic module 84 of AED 64 executes a self-diagnostic routine to acquire status information about AED 64 (104). In the example of FIG. 4, AED 64 generates an inspection indication (106), which requests a physical inspection of AED 64. AED 64 may generate an inspection indication when the diagnostic routine indicates a matter that calls for an inspection, or when electrodes associated with AED 64 have surpassed their shelf life, or when there are other circumstances calling for an in-person examination of AED 64. AED 64 communicates the device status information and inspection indication to docking station 66 (108), which in turn conveys the status information and inspection indication to status monitor 62 (110). Status monitor 62 receives the status information and inspection indication (112). In response to the inspection indication, status monitor 62 generates a service call (114) so that an inspection can be conducted. Until an inspection is conducted and AED is determined by service personnel to be fit for service, status monitor 62 can deem AED 64 to be out of service and display such status on status indicators 88 or 94.

Status monitor 62 may also interrogate docking station 66 by transmitting an interrogation for status information (116). As with interrogations for AED status information, status monitor 62 may initiate the interrogation in response to a command or automatically. Docking station 66 receives the interrogation executes a self-diagnostic routine to acquire status information about docking station 66 (118). Docking station 66 communicates the status information to status monitor 62 (120). Status monitor 62 receives the status information (122).

When status monitor 62 receives the AED status information and the docking station status information, status monitor may update a status log (124). The status log, which may be stored in memory 82, may include status information pertaining to the readiness of AED 64 and docking station 66. The status log may also record inspection certifications, inspection indications, history of usage or information pertaining to maintenance, and the like. When status information received in response to an interrogation indicates a matter requiring prompt attention, status monitor 62 may generate an alarm (126) to notify the responsible person that corrective action, such as urgent repair or maintenance, may be required.

Figure 5:
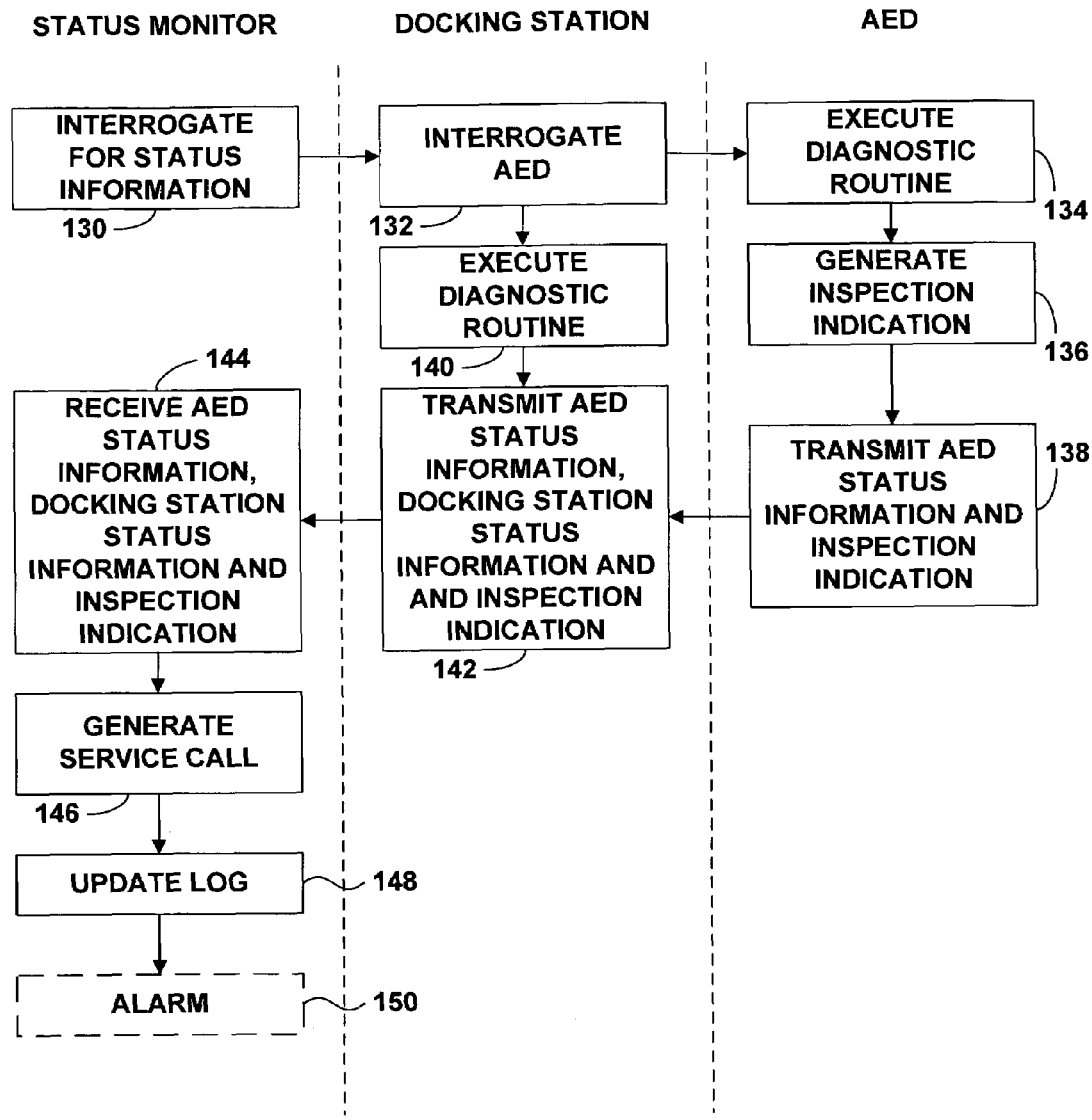
FIG. 5 is a flow diagram illustrating interrogation of a medical device according to an alternate embodiment of the invention.

FIG. 5 is a flow diagram illustrating an alternative interrogation technique in a system such as system 60. FIG. 5 is similar to FIG. 4, with a principal difference being that, in FIG. 5, diagnostic operations of AED 64 and docking station 66 are performed in parallel. Status monitor 62 may communicate an interrogation to docking station 66 (130). The interrogation may request AED status information, docking station status information, or status information from both devices. Upon receipt of the interrogation, docking station 66 generates an interrogation for AED status information, and submits the interrogation to AED 64 (132). In response to the interrogation, AED 64 executes a self-diagnostic routine to acquire AED status information (134). In FIG. 5, it is assumed that AED 64 generates an inspection indication (136) as a result of execution of the self-diagnostic routine. AED 64 communicates the status information and inspection indication to docking station 66 (138). In parallel, docking station 66 carries out self-diagnostic tests to acquire docking station status information (140). Docking station 66 communicates the status information and inspection indication to status monitor 62 (142), and status monitor 62 receives the status information and inspection indication (144). Status monitor may generate a service call (146) and update the status log (148) as described above, and may generate an alarm (150) when appropriate.

Other emergency medical devices and docking stations in system 60 may be interrogated in a similar fashion. Status monitor 62 may, for example, submit simultaneous interrogations to all AEDs and docking stations in system 60. Status monitor 62 may also interrogate AEDs and docking stations in system 60 in turn.

Figure 6:
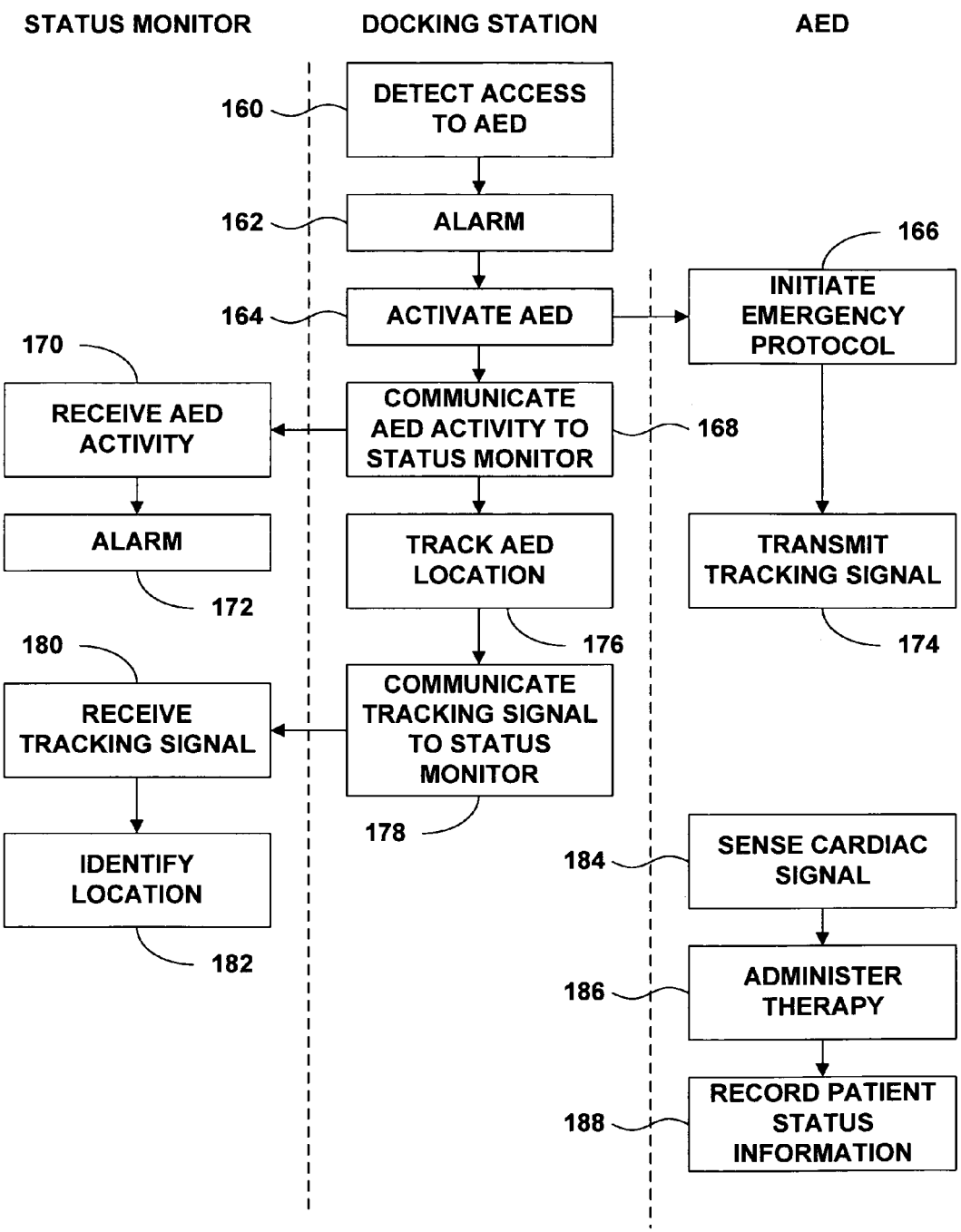
FIG. 6 is a flow diagram illustrating exemplary procedures triggered when a user accesses an emergency medical device associated with a docking station, according to an embodiment of the invention.

FIG. 6 is a flow diagram illustrating operation of a system such as system 60 when a user obtains access to an emergency medical device such as AED 64 (160). Access may be detected via sensor 71, and may be triggered by activity such as opening of a door on docking station 66 or removal of AED 66 from docking station 66. Assuming no valid authorization has been received, docking station optionally activates an alarm (162), which indicates that AED 64 has been accessed. The alarm can indicate not only the occurrence of an emergency situation, but also mischief on the part of the user that has accessed AED 64. In general, it is assumed that the alarm is genuine and that AED 64 as been accessed because of an emergency.

Docking station 66 communication interface 70 communicates a command to AED 64 that activates AED 64 (164). The command can be in the form of a wireless activation command, for example. In response, AED 64 initiates an emergency protocol (166), in which AED 64 powers up and prepares for use. Initiation of emergency protocol can include, for example, activating voice commands that instruct the user what to do when the user reaches the patient.

Docking station 66 also communicates the activity to status monitor 62 (168), which receives notification that AED 64 has been accessed (170). Status monitor 62 can activate an alarm (172) that notifies responders such as security personnel or emergency responders that an emergency is in progress.

When AED 64 becomes activated, AED 64 can begin transmitting a tracking signal (174) via trackable element 73. In some embodiments of the invention, trackable element 73 need not be specifically activated. When trackable element 73 is an RFID tag, for example, trackable element 73 is activated by a tracking element, rather than by AED 64. In some embodiments, docking station 66 tracks the location of AED 64 (176) and generates a tracking signal as a function of the position of AED 64 with respect to docking station 66. Docking station 66 can communicate the tracking signal to status monitor 62 (178). Status monitor 62 receives the tracking signal (180) from docking station 66, and may also receive tracking signals from other tracking elements as well. Status monitor 62 identifies the location of AED 64 as a function of one or more tracking signals (182). Status monitor 62 can notify responders of the location of AED 64.

When AED 64 is used with a patient, AED 64 senses cardiac signals (184), such as signals pertaining to the patient's heart rate and rhythm. When appropriate, AED 64 administers therapy (186), e.g., by delivering one or more defibrillation shocks. AED 64 records in memory 86 information pertaining to the cardiac signals and the therapy as patient status information (188). AED 64 will typically communicate the patient status information to status monitor 62 upon being returned to docking station 66.

Figure 7:
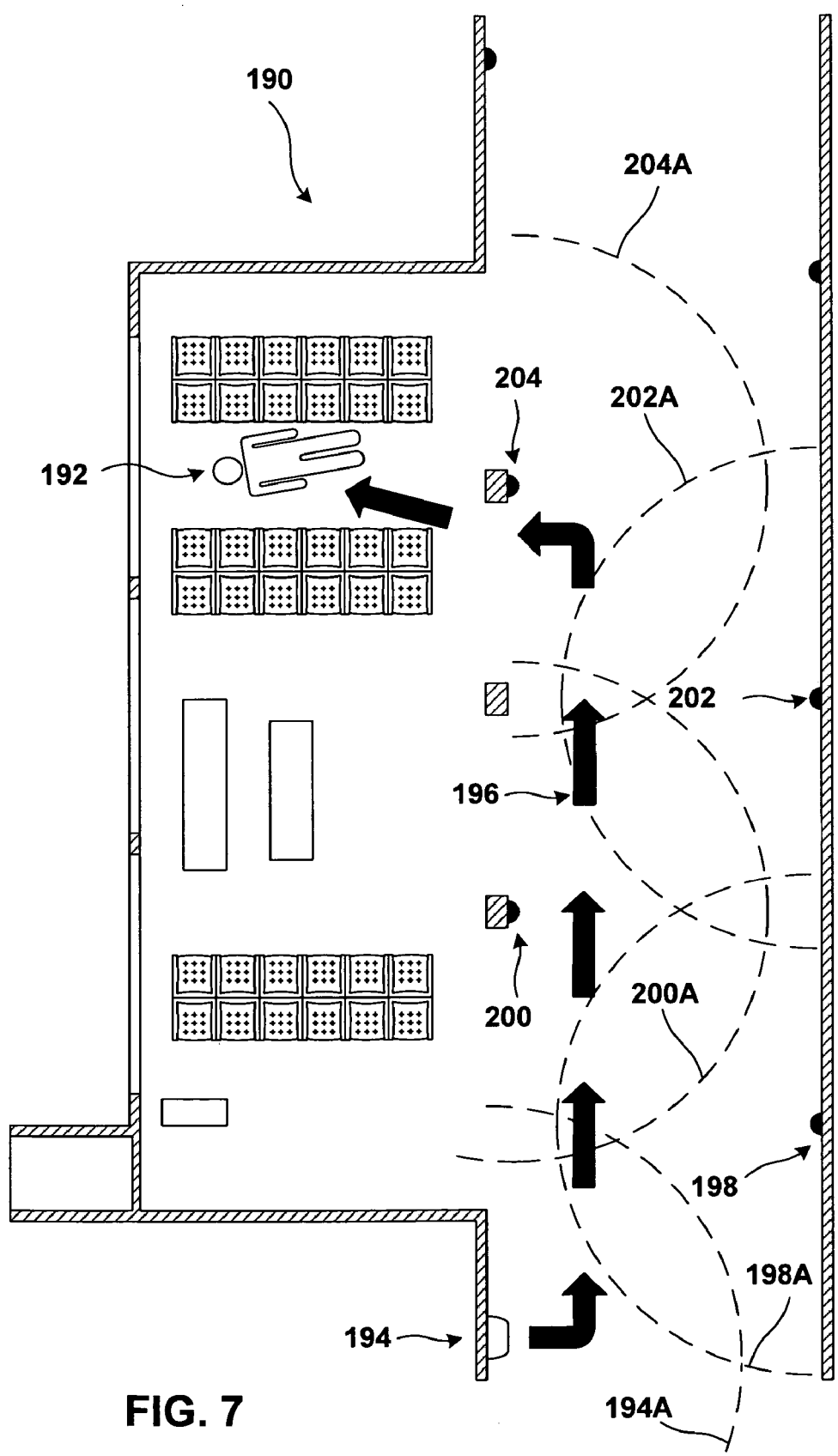
FIG. 7 is a schematic view of an exemplary venue, illustrating an exemplary deployment of a docking station with an emergency medical device and tracking elements, according to an embodiment of the invention.

FIG. 7 is a schematic view of an exemplary venue 190, such as a waiting room in an airport terminal. Patient 192 is in need of care, and may not be easily visible from more than a few meters away. A user retrieves an AED from a docking station 194 and transports the AED to patient 192 via path 196.

For purposes of illustration, the AED includes a trackable element in the form of an RFID tag. Docking station 194 includes a tracking element in the form of an RFID detector. Reference numeral 194A indicates the read area of the tracking element in docking station 134. In addition to the tracking element in docking station 194, there is a plurality of tracking elements 198, 200, 202, 204 deployed in venue 190. Docking station 194 and tracking elements 198, 200, 202, 204 are in communication with a remote status monitor (not shown in FIG. 5) via a network such as network 74 in FIG. 3. Path 196 of the user passes through read areas 198A, 200A, 202A and 204A of tracking elements 198, 200, 202 and 204. Each tracking element generates a tracking signal, which is communicated to the status monitor. The status monitor identifies the location of the AED as a function of the tracking signals, and can present the location to a person. The status monitor can, for example, notify responders of the location of the AED. As a result, responders can more quickly find patient 192 even though patient 192 may be difficult to locate visually.

Figure 8:
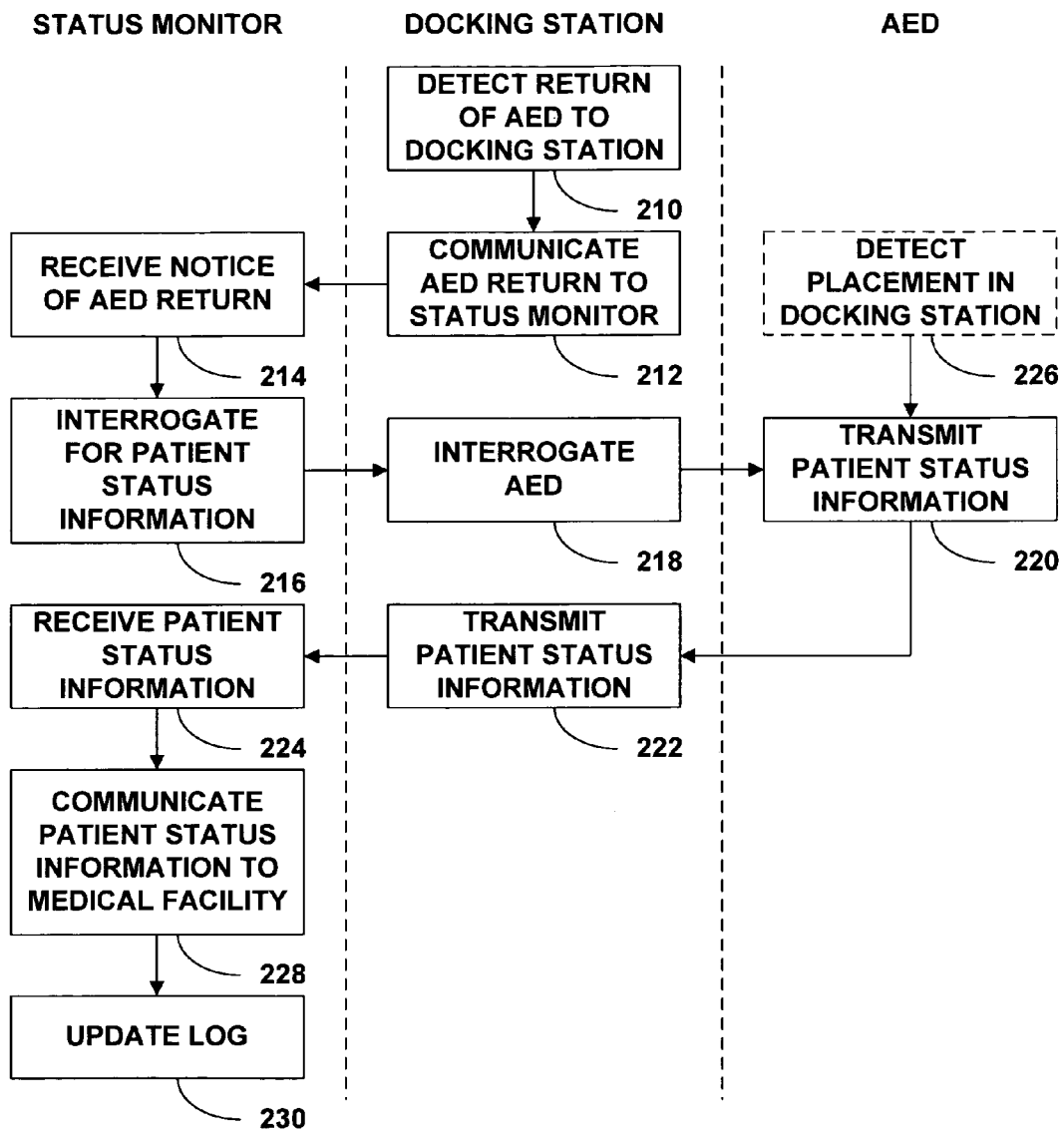
FIG. 8 is a flow diagram illustrating processes initiated by replacement of an emergency medical device in a docking station, according to an embodiment of the invention.

FIG. 8 is a flow diagram illustrating operation of a docking station in a system such as system 60 when a user places an emergency medical device such as AED 64 back in the docking element of a docking station such as docking station 66. When docking station 66 detects the return of AED 64 via sensor 71 (210), docking station 66 communicates a notice to status monitor 62 that AED 64 has been returned (212). Upon receiving the notice (214), status monitor 62 communicates an interrogation for patient status information (216), which docking station 66 passes on to AED 64 (218). In response, AED 64 communicates the patient status information to docking station 66 (220), which passes the patient status information to status monitor 62 (222, 224).

In an alternative implementation, AED 64 initiates the communication of patient status information without an interrogation. When AED 64 detects its placement in the docking element of docking station 66 (226), AED 64 communicates the patient status information to docking station 66 (220), which passes the patient status information to status monitor 62 (222, 224). In some situations, such as situations in which AED 64 is taken to a patient but is not used, AED 64 may have no patient status information. In such situations, AED 64 may communicate that it has no patient status information.

When status monitor 62 receives patient status information, status monitor 62 can communicate the patient status information to a medical facility (228). Status monitor 62 can further update a status log (230) by, for example, recording the history of usage of AED 64.

Upon detection of replacement of AED 64 in docking station 66 (210), docking station 66 can also interrogate AED 64 for device status information, using techniques such as those described above in connection with FIGS. 4 and 5. As a result, AED 64 communicates patient status information and device status information when replaced in docking station 66.

Figure 9:
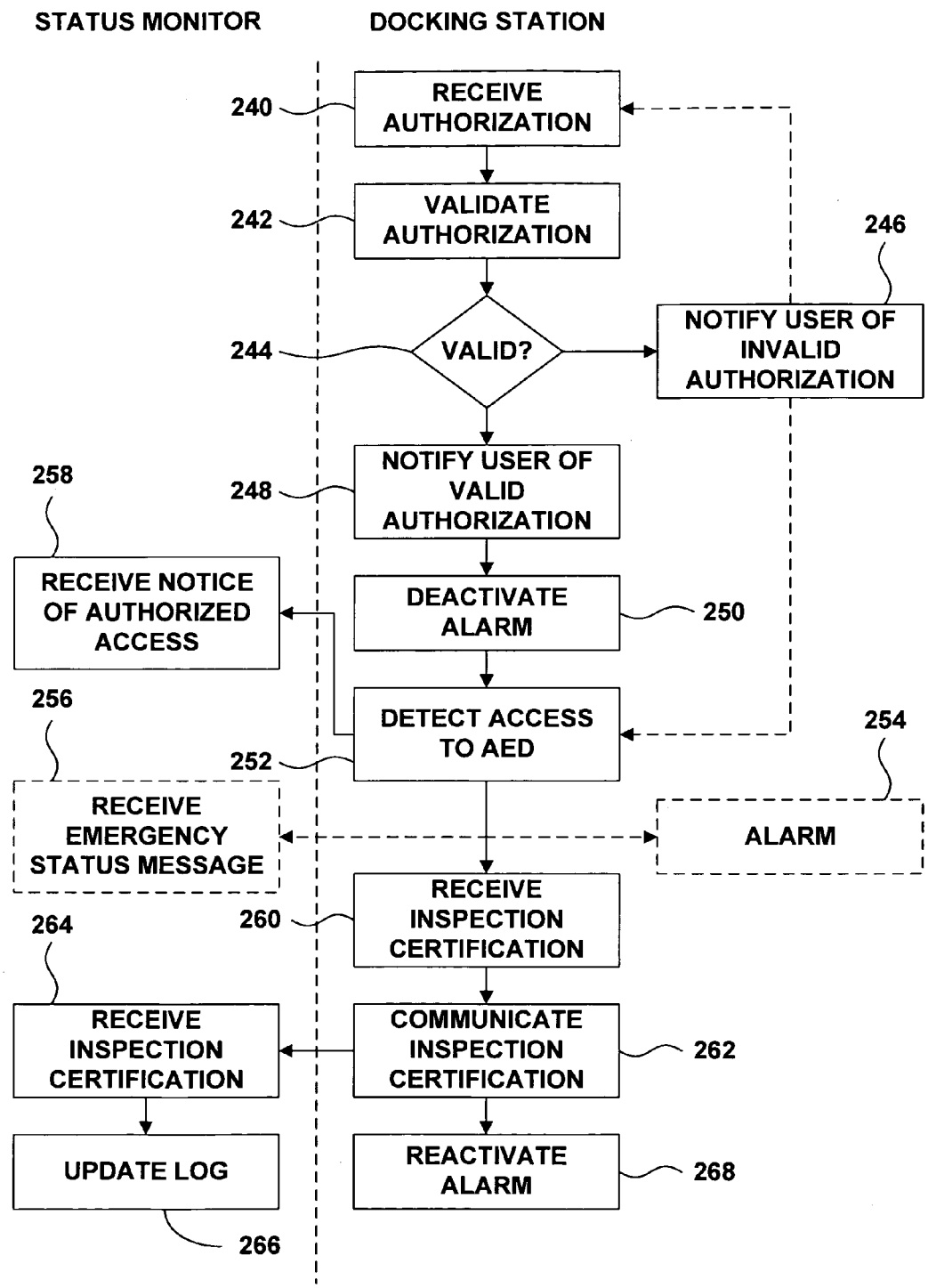
FIG. 9 is a flow diagram illustrating processes associated with authorized access to an emergency medical device in a docking station, according to an embodiment of the invention.

FIG. 9 is a flow diagram illustrating operation of a docking station such as docking station 66 in response to an authorization. When an authorized user such as a security personnel or service personnel wishes to have access to AED 64 without triggering an alarm, the authorized user enters an authorization via user input interface 69. In this way, docking station 66 receives an authorization (240). Docking station processor 67 validates the received authorization (242), determining whether the authorization is an authentic, recognized authorization. When the authorization is invalid (244), docking station 66 notifies the user that the authorization is invalid (246) via status indicators 94. The user may try again to enter a valid authorization (240). When the authorization is valid (244), docking station 66 notifies the user via status indicators 94 that the authorization is valid (246). Docking station 66 deactivates alarms (250) that would ordinarily sound when AED 64 is accessed, and may notify the user via status indicators 94 that the alarms have been deactivated.

In FIG. 9, docking station 66 performs the validation of the authorization. The invention also supports embodiments in which docking station 66 communicates the received authorization to status monitor 62, and status monitor 62 validates the authorization.

Docking station 66 detects access to AED 64 via sensor 71 (252). When a valid authorization has not been received, the alarm has not been deactivated, so docking station 66 activates an alarm (254) and communicates an emergency message to status monitor 62 (256). When docking station 66 is receives a valid authorization, however, access to AED 64 is not deemed to be an emergency. Docking station 66 communicates an administrative message to status monitor 62 that an authorized user is accessing AED 64 (258). In response, status monitor 62 may record that AED 64 is temporarily out of service.

When the authorized user has completed work and is ready to return AED 64 to service, the authorized user enters an inspection certification via user input interface 69, and docking station 66 receives the inspection certification (260). Although not shown FIG. 9, docking station 66 or status monitor 62 can validate the inspection certification for correctness, and can notify the user whether the inspection certification is correct or not. Validation of an inspection certification can be similar to validation of an authorization, as depicted in FIG. 9. When the inspection certification is invalid, docking station 66 or status monitor 62 can generate an alert that draws the attention of the authorized person to the invalid inspection certification. Docking station 66 communicates the inspection certification to status monitor 62 (262).

When status monitor 62 receives a valid inspection certification (264), status monitor 62 updates the status log (266) to reflect that AED 64 has been inspected and has been certified as ready for service. Docking station 66 reactivates the alarm (268). AED 64 is back in service.

The invention is not limited to the specific devices in system 60 shown in FIG. 3, but may be adapted to other systems as well. For example, the invention supports embodiments in which AED 64 communicates with status monitor 62 directly, rather than via docking station 66. In this variation, AED communication interface 68 is coupled to network 74 and to docking station communication interface 70. Docking station 66 can communicate with status monitor 62 via AED 64, or can communicate with status monitor 62 without using AED 64 as an intermediary.

The invention also supports both two-way communication and one-way communication among status monitor 62, AED 64 and docking station 66. For example, communication interface 70 of docking station 66 may receive one-way communication from status indicator 88 in AED 64. One-way communication may include, for instance, sensing whether an annunciator on AED 64 is illuminated or not.

Advantageously, the invention is not limited to any particular system. Rather, the invention may be practiced with systems of limitless configurations. Any number of docking stations and AEDs may be tracked, monitored and maintained with the invention.

Moreover, the invention is not limited to docking stations and AEDs, but may include any emergency medical device. For example, the invention may be practiced with a portable stroke apparatus, or a chest compression device, or a first aid kit, or other medical device. The invention may be practiced with an external defibrillator that is not an AED. A docking station may be associated with any of these medical devices. The docking stations themselves may include any assortment of cabinets, chests, brackets, clasps, bins, closets, kiosks, pedestals and other retaining devices that may be associated with one or more medical devices. In some embodiments, a single docking station may be associated with two or more medical devices. The invention may be practiced in a system that includes a variety of docking stations and a variety of medical devices.

The invention may also be practiced with any number of networks. The invention may be integrated into an existing security network or a private building maintenance network, for example. The invention does not require that all communication links be two-way links. The invention may be practiced with any combination of communication links. In some embodiments, the paths of communication may be restricted, e.g., to prevent misuse or inadvertent or improper programming of a medical device in the system.

The invention may provide other advantages as well. A responsible person may easily monitor the status or location of any number of medical devices deployed throughout a venue. Presentation of medical device status information and docking station status information at a status monitor may simplify inspection. A responsible person may, at a glance, determine whether any devices in the system are out of service or in need of attention. Record keeping operations, such as maintenance of a status log, are also simplified by a networked system.

In the event of a problem with any device in the system, the invention facilitates prompt notification of the responsible person. The output elements on the medical devices and the docking stations may alert the responsible person to the problem. In addition, the medical devices or the docking stations can generate an inspection indication that is communicated to the status monitor, which in turn alerts the responsible person to the problem. A remote alert at a monitoring site and a local alert at the site of the device cooperate to improve the likelihood that the problem will be noticed and addressed. In addition, some embodiments of the invention provide for interrogation of a medical device or a docking station, prompting the device to execute a self-diagnostic routine that may discover a problem not previously observed, and as a consequence, generate an inspection indication.

In an emergency, the invention may utilize status information to assist with handling the emergency. When an operator retrieves a medical device such as an AED from a docking station, for example, the docking station may immediately communicate that fact to the status monitor. A responsible person may promptly dispatch security or emergency personnel to the general area in which the personnel may be needed. The docking station may also issue an audible alarm that may summon security or emergency personnel to the general site of the emergency. The invention may also advantageously supply status information to docking stations that may assist in an emergency, such as the location of the nearest medical devices that are in service.

Various embodiments of the invention have been described. These specific embodiments are illustrative of the practice of the invention. Various modifications may be made without departing from the scope of the claims. For example, the invention is not limited to AEDs and docking stations, but may be practiced with a variety of medical devices. There may be advantages to deploying the medical devices with docking stations, e.g., to deter mischief and to handle energy consuming operations such as communications. The invention is not limited, however, to medical devices that are associated with docking stations. The invention may encompass, for example, a networked set of emergency medical devices, some of which are associated with no docking station.

The invention is not limited to systems in which medical devices or docking stations are deployed in fixed locations. In some instances, it may be beneficial to deploy a docking station in a mobile platform, such as an ambulance or a vehicle used by a security guard. Moreover, the invention includes embodiments in which a remote unit such as a status monitor is mobile.

Many examples of communication techniques are described for communication among medical devices, docking stations and a status monitor. The invention is not limited to the techniques explicitly described. Communication may be based upon optical communication links, magnetic communication links, infrared communication links, or visual status change detectors. Furthermore, several radio frequency communication links have been described, but the invention is not limited to the techniques explicitly described. A cellular telephone link, for example, may employ any recognized communication protocol, such as code division multiple access (CDMA), Global System for Mobile Communications (GSM), or General Packet Radio Service (GPRS).

Furthermore, the above description is not intended to describe the exclusive functionality of the devices. For example, a docking station or a medical device such as an AED may, for example, maintain a status log separate from the status log, if any, maintained by the status monitor. A docking station may additionally serve as a recharging station in which a medical device may recharge on-board batteries.

Moreover, the invention includes software to carry out the techniques described herein. The invention may be embodied as a computer-readable medium that includes instructions for causing a programmable processor to carry out the methods described above. A "computer-readable medium" includes but is not limited to read-only memory, Flash memory and a magnetic or optical storage medium. The instructions may be implemented as one or more software modules, which may be executed by themselves or in combination with other software.

The instructions and the media are not necessarily associated with any particular computer or other apparatus, but may be carried out by various general-purpose or specialized machines. The instructions may be distributed among two or more media and may be executed by two or more machines. The machines may be coupled to one another directly, or may be coupled through a network.

The invention may also be embodied as one or more devices that include logic circuitry to carry out the functions or methods as described above. The logic circuitry may include a processor that may be programmable for a general purpose or may be dedicated, such as microcontroller, a microprocessor, a Digital Signal Processor (DSP), Application Specific Integrated Circuit (ASIC), and the like. These and other embodiments are within the scope of the following claims.

The invention claimed is:

1. A method comprising:
   receiving at an emergency medical device an inspection certification from an inspector via a user interface of the emergency medical device;
   receiving at a docking station the emergency medical device, wherein the docking station comprises a communication interface; and
   receiving at the communication interface of the docking station the inspection certification from the emergency medical device.

2. The method of claim 1, further comprising communicating the inspection certification from the docking station to a remote unit.

3. The method of claim 1, further comprising:
   validating the inspection certification to determine whether the inspection certification is invalid; and
   generating an alert when the inspection certification is invalid.

4. A method comprising:
   receiving at an emergency medical device an inspection certification from an inspector via a user interface of the emergency medical device;
   receiving in a docking station the emergency medical device; and
   receiving at the docking station the inspection certification from the emergency medical device,
   wherein the inspection certification comprises an identification code that identifies the inspector of the emergency medical device.

5. A method comprising:
   using an emergency medical device to treat a patient;
   after using the emergency medical device, placing the emergency medical device in a docking station; and
   in response to the emergency medical device being placed in the docking station after being used to treat a patient:
      establishing communication with a remote unit via a communication network; and
      communicating an inspection indication to the remote unit, the inspection indication requesting a physical inspection for the emergency medical device.

6. The method of claim 5, further comprising communicating emergency medical device status information to the remote unit.

7. The method of claim 5, wherein the emergency medical device comprises an external defibrillator.

\* \* \* \* \*

UNITED STATES PATENT AND TRADEMARK OFFICE
CERTIFICATE OF CORRECTION

| | | |
|---|---|---|
| PATENT NO. | : 7,510,526 B2 | |
| APPLICATION NO. | : 11/027766 | |
| DATED | : March 31, 2009 | |
| INVENTOR(S) | : Merry et al. | |

It is certified that error appears in the above-identified patent and that said Letters Patent is hereby corrected as shown below:

Column 1, line 38, "ready provide" should read -- ready to provide --

Column 11, line 26, "wifeless" should read -- wireless --

Column 14, line 13, "two way" should read -- two-way --

Column 14, line 14, "6" should read -- 62 --

Column 16, line 58, "as" should read -- has --

Column 18, lines 52-53, "is receives" should read -- receives --

Signed and Sealed this
Nineteenth Day of July, 2011

David J. Kappos
*Director of the United States Patent and Trademark Office*